United States Patent
Boeckh et al.

(10) Patent No.: US 7,767,425 B2
(45) Date of Patent: Aug. 3, 2010

(54) ENZYMATIC SYNTHESIS OF SUGAR ACRYLATES

(75) Inventors: Dieter Boeckh, Limburgerhof (DE); Bernhard Hauer, Fußgönhein (DE); Dietmar Häring, Ludwigshafen (DE)

(73) Assignee: BASF Aktiengesellschaft (DE)

( * ) Notice: Subject to any disclaimer, the term of this patent is extended or adjusted under 35 U.S.C. 154(b) by 1337 days.

(21) Appl. No.: 10/495,580

(22) PCT Filed: Nov. 15, 2002

(86) PCT No.: PCT/EP02/12840

§ 371 (c)(1), (2), (4) Date: Mar. 14, 2005

(87) PCT Pub. No.: WO03/042227

PCT Pub. Date: May 22, 2003

(65) Prior Publication Data

US 2006/0035341 A1    Feb. 16, 2006

(30) Foreign Application Priority Data

Nov. 16, 2001   (DE) ............................... 101 56 352

(51) Int. Cl.
*C12P 19/02* (2006.01)

(52) U.S. Cl. .................. 435/105; 435/183; 435/196; 435/195

(58) Field of Classification Search .................. 435/100, 435/105, 183, 196, 195
See application file for complete search history.

(56) References Cited

U.S. PATENT DOCUMENTS 5,240,835 A   8/1993   Pettrone et al.

FOREIGN PATENT DOCUMENTS

| JP | 11-028096 | 2/1999 |
|---|---|---|
| WO | WO94/14823 | 7/1994 |

OTHER PUBLICATIONS

Bourg-Garros et al. "Optimization of lipase-catalyzed sysnthesis . . . " Enzyme Microbial Technol. (1998) 22: 240-245.*

De Goede, A.T.J.W., et al., "Selective lipase-catalyzed 6-0-acylation of alkyl α-D-glucopyranosides using functionalized ethyl esters", Recueil des Travaux Chimiques des Pays-Bas, vol. 112, Nov. 1993, pp. 567-572, XP008022342.

Park, Hyun Gyu and Ho Nam Chang, "Enzymatic regioselective synthesis of sucrose acrylate esters", Biotechnology Letters, vol. 22, No. 1, Jan. 2000, pp. 39-42, XP002255426.

Martin, Brett D., et al., "Biocatalytic Synthesis of Sugar-Containing Poly(acrylate)-Based Hydrogels", Macromolecules, vol. 25, No. 26, Dec. 21, 1992, pp. 7081-7085, XP002255427.

De Goede, A.T.J.W., et al, "Selective Lipase-Catalyzed Esterification of Alkyl Glycosides", Biocatalysis, vol. 9, 1994, pp. 145-155, XP008022345.

Kumar, Rajesh and Richard A. Gross, "Biocatalytic Route to Well-Defined Macromers Built around a Sugar Core", Journal of the American Chemical Society, vol. 124, No. 9, Mar. 6, 2002, XP002255428; and Kumar, Rajesh and Richard A. Gross, "Biocatalytic Route to Well-Defined Macromers Built Around a Sugar Core", Journal of the American Chemical Society, (Supporting Information), 2002, pp. S1-S7, XP002255429.

Li, Yanzi and David G. Rethwisch, "Scale-Up of Pseudo Solid-Phase Enzymatic Synthesis of α-Methyl Glucoside Acrylate", Biotechnology and Bioengineering, vol. 79, No. 1, Jul. 5, 2002, pp. 15-22, XP002255430.

Ikeda, Isao and Alexander M. Klibanov, "Lipase-Catalyzed Acylation of Sugars Solubilized in Hydrophobic Solvents by Complexation", Biotechnology and Bioengineering, vol. 42, No. 6, Sep. 5, 1993, pp. 788-791, XP002025123.

Chen, X, et al., "Enzymatic and chemoenzymatic approaches to synthesis of sugar-based polymer and hydrogels", Carbohydrate Polymers, vol. 28, No. 1, 1995, pp. 15-21, XP004034426.

Chen, Xiaomao, et al., "Chemoenzymatic synthesis of linear poly(sucrose acrylate): optimization of enzyme activity and polymerization conditions", Macromol. Chem. Phys., 1994, vol. 195, pp. 3567-3578.

Chan, Anita Wai-Yin and Bruce Ganem, "A Regioselective, Chemoenzymatic Synthesis of Sucrose-1'-Methacrylate", Biocatalysis, 1993, vol. 8, pp. 163-169.

Ivanova, N.P., et al., "The Use of Alkaline Protease for Obtaining Unsaturated Sugar Monoesters", Prikladnaya biokhimia i mikrobiologya, 1997, vol. 33, pp. 269-274 (with English abstract).

Panarin, E.F., et al., "Enzymatic Synthesis of Vinyl Saccharide and Related Polymers", Vysokomolekulyarnye Soedineniya Seriya A & Seriya B, 1998, vol. 40, pp. 15-23 (with English abstract).

Potier, P., et al., "Proteinase N-catalysed transesterifications in DMSO-water and DMF-water: preparation of sucrose monomethacrylate", Tetrahedron Letters, 2000, vol. 41, pp. 3597-3600.

De Goede, A.T.J.W., et al., "Selective Acylation of Sugar Derivatives Catalyzed by Immobilized Lipase", Heterogeneous Catalysis and Fine Chemicals III (Editors. Guisnet et al.), Elsevier Science Publishers, 1993, pp. 513-520.

* cited by examiner

*Primary Examiner*—Irene Marx
*Assistant Examiner*—Susan Hanley
(74) *Attorney, Agent, or Firm*—Connolly Bove Lodge & Hutz LLP

(57) ABSTRACT

A process is described for the enzymatic synthesis of sugar acrylates, and a process is described for preparing polymeric sugar acrylates, the polymers obtainable by this process and their use for preparing, for example, cosmetics, drugs, laundry detergents, thickeners, protecting colloids, superabsorbents and textile sizes.

15 Claims, No Drawings

ENZYMATIC SYNTHESIS OF SUGAR ACRYLATES

RELATED APPLICATIONS

This application is a national stage application (under 35 U.S.C. 371) of PCT/EP02/12840 filed Nov. 15, 2002, which claims benefit of German application 101 56 352.3 filed Nov. 16, 2001.

FIELD OF THE INVENTION

The invention relates to a process for the enzymatic synthesis of sugar acrylates and to a process for preparing polymeric sugar acrylates, the polymers obtainable by this process and their use for preparing, for example, cosmetics, drugs, laundry detergents, thickeners, protecting colloids, superabsorbents and textile sizes.

DESCRIPTION OF THE BACKROUND

The sugar acrylates are accessible in various ways. Targeted chemical synthesis of sugar acrylates is difficult because of the high functionality of the sugar molecules. Using protecting groups, complex and expensive multistage syntheses of monoacrylic esters of various sugars have been described. Direct esterification or transesterification of acrylic acid or acrylic esters with sugars leads to monoacrylic esters of the sugar only with relatively low conversion rates (<20%). At relatively high conversion rates, nonselective formation of multiple esters occurs. These can only be separated by complex chromatographic methods. Although with the use of activated acrylic acid derivatives, for example acryloyl chloride, the reaction times can be shortened, this also leads to nonselective esterification of the sugars.

In the case of biocatalytic synthesis, hitherto essentially two different routes have been followed. The first preparation pathway proceeds via the use of activated (meth)acrylic acid derivatives. In particular, syntheses have been described using vinyl (meth)acrylate (for example Chen et al., *Macromol. Chem. Phys.* 1994, 195, 3567-3578; Chan and Ganem, *Biocatalysis* 1993, 8, 163-169; Park and Chang, *Biotechnol. Lett.* 2000, 22, 39-42; Ivanova et al., *Prikladnaya biokhimia i mikrobiologya* 1997, 33, 269-274);

butanediol monooxime esters of (meth)acrylic acid (Panarin et al., *Vysokomolekulyarnye Soedineniya Seriya A & Seriya B* 1998, 40, 15-23); or trifluoroethyl (meth)acrylate (Potier et al., *Tetrahedron Lett.* 2000, 41, 3597-3600).

Activated acrylic acid derivatives of this type, because of their high manufacturing costs, are not of interest for economic synthesis of sugar acrylates.

The second pathway for the biocatalytic preparation of sugar acrylates proceeds by the enzymatic transesterification of alkyl glucosides with alkyl acrylates (Goede et al., *Biocatalysis* 1994, 9, 145-155; Goede et al., *Recl. Trav. Chim. Pays-Bas* 1993, 112, 567-572; Goede et al., *Heterogeneous Catalysis and Fine Chemicals III* (Editors. Guisnet et al.) Elsevier Science Publishers 1993, pp 513-520).

The disadvantages of the syntheses described therein are considered to be:

a) large reaction volumes because of the use of low sugar concentrations (0.06-0.1 mol/l); b) the greater molar excess of acrylate (about 44-134 times excess); c) the greater volume fraction of organic solvent (addition of about 5 ml of tert-butanol per mmol of sugar).

JP-A-11028096 describes a special stirrer system for reacting sugars and having great differences in viscosity. Using "gate blades", the enzymatic reaction of alkylglucosides with alkyl acrylates successfully proceeds. In a comparative example (reaction of butyl glucoside with methyl acrylate) using a different stirrer, no reaction was obtained. In all of the examples the reaction proceeded without the addition of an organic solvent.

Disadvantages of this process are considered to be:

a) the use of a special stirrer as a prerequisite for the reaction, b) the great molar excess of methyl acrylate over sugar (42-52 fold), and c) the high reaction temperatures (preferably 50-80° C.) which cause rapid denaturation of enzymes and increased tendency of polymerization of acrylates, and require the addition of stabilizers; and d) the use of large amounts of enzyme (at least 10% by weight; in examples 20-100% by weight).

U.S. Pat. No. 5,240,835 describes the enzymatic synthesis of unsaturated polymerizable monomers from an unsaturated ester and an organic compound containing a primary or secondary hydroxyl group using a biocatalyst derived from *Corynebacterium oxydans*. The reaction proceeds in an aqueous environment without the presence of an organic solvent. The ester is preferably used in a high molar excess (about 50 to 120 fold). The successful conversion of sugars is not verified by a single example. The following are taken to be disadvantageous in this case: a) the requirement for isolating a specific enzyme from *C. oxydans*; and b) the high molar excess of ester to alcohol.

SUMMARY OF THE INVENTION

It is an object of the invention to develop a process for preparing sugar acrylates which at least partially avoids the above-described disadvantages of the prior art. The synthesis should be able to be carried out in particular with good yield of desired sugar monoacrylate selectively, that is to say without forming multiple esters, in an inexpensive manner.

We have found that the above object is achieved, surprisingly, by specific choice of the processing conditions, in particular by employing an organic solvent environment having a relatively low absolute content of organic solvent (based on the amount of sugar used).

DETAILED DESCRIPTION OF THE INVENTION

The invention firstly relates to a process for the enzymatic synthesis of sugar acrylates, which comprises reacting a sugar compound with an acrylic acid compound or an alkyl ester thereof in a liquid reaction medium comprising an organic solvent in the presence of an acrylate-transferring enzyme, the organic solvent being present in an amount of less than about 4.8 ml per mmol of sugar compound, and the sugar acrylate formed, after completion of the reaction, being isolated if appropriate from the reaction mixture.

The organic solvents used are preferably those which are selected from the group consisting of monools, such as $C_3$-$C_6$-alkanols, in particular tert-butanol and tert-amyl alcohol, pyridine, poly-$C_1$-$C_4$-alkylene glycol di-$C_1$-$C_4$-alkyl ethers, in particular polyethylene glycol di-$C_1$-$C_4$-alkyl ethers, for example dimethoxyethane, diethylene glycol dimethyl ether, polyethylene glycol dimethyl ether 500, $C_1$-$C_4$-alkylene carbonates, in particular propylene carbonate, $C_3$-$C_6$-alkyl acetates, in particular tert-butyl acetate, acetone, 1,4-dioxane, 1,3-dioxolane, THF, dimethoxymethane, dimethoxyethane, and their single-phase or multiphase mixtures.

The organic solvent is preferably used in an amount of from 0.01 to 4 ml/mmol, preferably from 0.1 to 3 ml/mmol of sugar compound. Optionally, aqueous solvents can be added to the organic solvents, so that, depending on the organic solvent, single-phase or multi-phase reaction solutions are formed. Examples of aqueous solvents are water and aqueous dilute (e.g. from 10 to 100 mM) buffers, for example having a pH in the range from about 6 to 8, for example potassium phosphate or TRIS-HCl buffer.

The substrates are present in the reaction medium either in dissolved form, suspended in solids or in an emulsion. Preferably, the initial sugar concentration is in the range of from about 0.1 to 20 mol/l, in particular from 0.15 to 10 mol/l, or from 0.2 to 5 mol/l.

The inventively used sugar compounds are open-chain and cyclic monosaccharides, oligosaccharides and polysaccharides, and also oxidized, reduced, alkylated, esterified, aminated sugars from natural and synthetic sources. In particular, the sugar compounds are selected from the group consisting of monosaccharides and oligosaccharides and the esterifiable derivatives thereof in an optically pure form or as a stereoisomer mixture. Esterifiable monosaccharides are selected from the group consisting of aldoses and ketoses, in particular aldopentoses and aldohexoses and ketopentoses and ketohexoses and the esterifiable derivatives thereof, in particular $C_1$-$C_{30}$-alkyl glycosides. Preferred oligosaccharides are selected from the group consisting of disaccharides and trisaccharides and the esterifiable derivatives thereof. Further possible sugars are $C_1$-$C_{30}$-alkyl glycosides containing one or more functional groups in the alkyl chain, and glycosides which bear polyalkylene glycol radicals, for example polyethylene glycol or polypropylene glycol radicals. Non-restricting examples of suitable functional groups are O-, S- or N-containing groups, such as HO, HS, amino, carboxyl or carbonyl and ether and thioether bridges.

Preferably, $C_1$-$C_{30}$-alkyl glycosides, for example $C_1$-$C_6$-alkyl glycosides, in particular methyl glycopyranosides, methyl-α-D-glucopyranoside, are used. The alkyl glycoside can be added directly or can be prepared in the reaction solution as an intermediate from the sugar together with the corresponding alkyl alcohol under acid catalysis (for example using ion exchangers).

The inventively used acrylic acid compound is preferably selected from the group consisting of (meth)acrylic acid, anhydrides, $C_1$-$C_6$-alkyl-substituted acrylic acid, the $C_1$-$C_6$-alkyl esters thereof or ethylene glycol diacrylates. Inventive acrylic acid compounds comprise not only unsubstituted but also substituted acrylic acids. Suitable substituents are $C_1$-$C_6$-alkyl groups, in particular methyl or ethyl groups. Preferably, (meth)acrylic acid or (meth)acrylic acid derivatives are used.

Suitable (meth)acrylic acid derivatives are esters with saturated and unsaturated, cyclic or open-chain $C_1$-$C_{10}$ monoalcohols, in particular methyl, ethyl, butyl and 2-ethylhexyl (meth)acrylate. The inventive $C_1$-$C_{10}$ monoalcohols preferably comprise $C_1$-$C_6$-alkyl groups of the above definition or their longer-chain unbranched or branched homologs having up to 10 carbon atoms or $C_4$-$C_6$-cycloalkyl groups, such as cyclopropyl, cyclopentyl or cyclohexyl which may be unsubstituted or substituted by one or more alkyl groups having 1 to 3 carbon atoms.

Unless otherwise stated, thus according to the invention $C_1$-$C_4$-alkyl is methyl, ethyl, n-propyl or isopropyl, n-, sec- or tert-butyl; $C_3$-$C_6$-alkyl is in particular n-propyl or isopropyl, n-, sec- or tert-butyl, n- or tert-amyl and unbranched or branched hexyl.

$C_1$-$C_6$-alkyl groups comprise the above definitions for $C_1$-$C_4$ and $C_3$-$C_6$-alkyl. $C_1$-$C_4$-alkylene is preferably methylene, ethylene, propylene or 1- or 2-butylene. $C_1$-$C_{30}$-Alkyl groups comprise the above $C_1$-$C_6$-alkyl groups and longer-chain radicals, for example n-heptyl, n-octyl, n-nonyl, n-decyl, n-undecyl, n-dodecyl, n-tridecyl, n-tetradecyl, n-pentadecyl and n-hexadecyl, octadecyl, docosanyl and the single branched or multiply branched analogs thereof.

According to the invention the molar ratio of acrylic acid compound to sugar compound can vary within a broad range, for example in the ratio from 100:1 to 1:10, in particular from 30:1 to 1:1. Preferably, acrylic acid compound is used in a molar ratio to sugar compound from about 10:1 to 1:1, in particular from about 3:1 to 10:1.

The enzymes used according to the invention are selected from the group consisting of hydrolases, preferably esterases (E.C.3.1.-.-), such as in particular lipases (E.C.3.1.1.3), glycosylases (E.C.3.2.-.-) and proteases (E.C.3.4.-.-) in free or immobilized form. Those which are particularly suitable are Novozyme 435 (lipase from *Candida antarctica* B) or lipase from *Aspergillus* sp., *Burkholderia* sp., *Candida* sp., *Pseudomonas* sp. or pig pancreas. The enzyme content in the reaction medium is in the range from about 0.1 to 10% by weight, based on the sugar compound used. In the conversion according to the invention, the enzymes may be used in the pure form or bound to a support (immobilized).

In the inventive processes, the reaction temperature is in the range from 0 to about 70° C., preferably from 20 to 60° C. The reaction time is usually in the range from about 1 to 72 hours. Any desired methods can be used to mix the reaction batch thoroughly. Special stirring apparatuses are not necessary. The reaction medium can be single-phase or multiphase and the reactants are dissolved, suspended or emulsified therein, if appropriate introduced together with the molecular sieve and the enzyme preparation is added to start the reaction. The temperature is set to the desired value during the reaction.

The process according to the invention may, however, also be carried out batchwise, semicontinuously or continuously in customary bioreactors. Suitable methods and bioreactors are known to those skilled in the art and described, for example, in Römpp Chemie Lexikon, 9th edition, Thieme Verlag, head word "bioreactor", or Ullmann's Encyclopedia of Industrial Chemistry, 5th edition, volume B4, pp 381 et seq., which is expressly incorporated herein by reference. Those skilled in the art will adapt the operating of the reactor and the procedure to the respective requirements of the desired esterification reaction.

Any alcohol produced during the transesterification can be removed continuously or stepwise from the reaction equilibrium in a suitable manner. Suitable methods for this are preferably molecular sieves (pore size for example in the range of about 3-10 Angström), or removal by distillation or using suitable semipermeable membranes. The reaction time is usually in the range from about 3 to 72 hours.

After the reaction is complete the desired sugar acrylate can if necessary be separated from the organic solvent, for example by chromatography, purified and then used to prepare the desired polymers.

The invention further relates to a process for preparing polymeric sugar acrylates, which comprises preparing at least one sugar acrylate in the above manner, separating off the sugar acrylate from the reaction mixture if necessary, and polymerizing it, if appropriate together with other comonomers.

Suitable other comonomers are: other inventively prepared sugar acrylates of the inventive type or polymerizable non-sugar monomers, such as (meth)acrylic acid, maleic acid, itaconic acid, alkali metal salts or ammonium salts thereof and esters thereof, O-vinyl esters of $C_1$-$C_{25}$ carboxylic acids, N-vinylamides of $C_1$-$C_{25}$ carboxylic acids, N-vinylpyrrolidone, N-vinylcaprolactam, N-vinyloxazolidone, N-vinylimidazole, (meth)acrylamide, (meth)acrylonitrile, ethylene, propylene, butylene, butadiene, styrene. Examples of suitable $C_1$-$C_{25}$ carboxylic acids are saturated acids, such as formic, acetic, propionic and n-butyric and isobutyric acid, n-valeric acid and isovaleric acid, caproic acid, oenanthic acid, caprylic acid, pelargonic acid, capric acid, undecanoic acid, lauric acid, tridecanoic acid, myristic acid, pentadecanoic acid, palmitic acid, margaric acid, stearic acid, nonadecanoic acid, arachidic acid, behenic acid, lignoceric acid, cerotic acid and melissic acid.

Such polymers are prepared, for example, in a similar manner to the processes described in general in "Ullmann's Encyclopedia of Industrial Chemistry, Sixth Edition, 2000, Electronic Release, head word: polymerization process". Preferably, the (co)polymerization is performed as free-radical polymerization in the form of solution, suspension, precipitation or emulsion polymerization or by polymerization without solvent.

The invention further relates to polymeric sugar acrylates which are obtainable in the above manner and to their use for preparing cosmetics, drugs, laundry detergents, thickeners, protecting colloids, superabsorbents and textile sizes, glues, paper, concrete or dispersions.

The invention will now be described in more detail with reference to the examples below.

The examples do not and should not be viewed as limiting the scope of the invention.

EXAMPLE 1

A mixture of 5 mmol (0.97 g) of methyl α-D-glucopyranoside, 50 mmol (4.3 g) of methyl acrylate, 5 ml of tert-butanol, 1 g of molecular sieve (5 Å) and 0.1 g of Novozym 435 (lipase from *Candida antarctica* B) was shaken for 24 h at 40° C. and 200 rpm. Silylation reagent (Sylon HTP) was added to one sample and the product was analyzed by gas chromatography (GC). Analysis found 78% methyl 6-O-acryloylglucopyranoside, 22% methyl glucopyranoside and <1% polyesterified sugars.

EXAMPLE 2

20 mmol (3.9 g) of methyl α-D-glucopyranoside, 200 mmol (17.2 g) of methyl acrylate, 20 ml of acetone and 0.4 g of Novozym 435 were stirred with a magnetic stirrer bar in a 100 ml Soxhlet apparatus under reflux. To remove the resultant methanol, the extraction space was charged with 5 g of molecular sieve (5 Å) in 100 ml of acetone. After 24 h, the supernatant was decanted off from the molecular sieve, the acetone was removed in vacuo and the oily residue (1.26 g) was analyzed by GC. Analysis found 87% methyl 6-O-acryloylglucopyranoside, 13% methyl glucopyranoside and <1% polyesterified sugars.

EXAMPLE 3

50 mmol (9.7 g) of methyl α-D-glucopyranoside, 500 mmol (43.0 g) of methyl acrylate, 50 ml of dimethoxyethane, 12.5 g of molecular sieve (5 Å) and 1.0 g of Novozym 435 were stirred at 60° C. After 24 h the mixture was filtered off and the filtrate was concentrated in vacuo. The residue (8.92 g) was analyzed by GC. Analysis found 84% methyl 6-O-acryloylglucopyranoside, 16% methyl glucopyranoside and <1% polyesterified sugars.

EXAMPLE 4

50 mmol (9.7 g) of methyl α-D-glucopyranoside, 500 mmol (43.0 g) of methyl acrylate, 50 ml of acetone, 12.5 g of molecular sieve (5 Å) and 1.0 g of Novozym 435 were stirred at 60° C. After 24 h the mixture was filtered off and the filtrate was concentrated in vacuo. The residue (4.91 g) was analyzed by GC. Analysis found 94% methyl 6-O-acryloylglucopyranoside, 6% methyl glucopyranoside and <1% polyesterified sugars.

EXAMPLE 5 a) 0.75 mol (145.6 g) of methyl α-D-glucopyranoside, 7.5 mol (645.7 g) of methyl acrylate, 750 ml of acetone, 187.5 g of molecular sieve (5 Å), 161 mg of phenothiazine and 15.0 g of Novozym 435 were stirred at 60° C. After 24 h the mixture was filtered off and the filtrate was concentrated in vacuo. The residue (91.7 g) was analyzed by GC. Analysis found 92% methyl 6-O-acryloylglucopyranoside, 5% methyl glucopyranoside and 3% of a diacrylate of methyl glucopyranoside.

b) The amount of molecular sieve was reduced to 60 g in the above batch and 59.9 g of residue were obtained. GC analysis found a composition of 92% methyl 6-O-acryloyl-glucopyranoside, 7.6% methyl glucopyranoside and 0.4% of a diacrylate of methyl glucopyranoside.

EXAMPLE 6 a) Comparative Experiments With Ethyl Acrylate

To further illustrate the surprising effect associated with the inventive teaching, the following comparative experiments were carried out. For this the reaction batches (A) to (E) described below were reacted.

| Batch (A), prior art (see Goede et al. loc. cit. 1993) | |
|---|---|
| 5 mmol | methyl α-D-glucopyranoside (0.971 g) |
| 223.7 mmol | ethyl acrylate (22.4 g; 24.3 ml) |
| 24.3 ml | tert-butanol |
| 97.3 mg | Novozym 435 |
| 1.94 g | 5 Å molecular sieve |

Shake for 72 h at 40° C.
The conversion rate was determined by GC after silylation.

Comparison batches (B) to (E) (conditions as specified under (A) unless otherwise stated):

| Batch (B) | |
|---|---|
| 50 mmol | ethyl acrylate (5.01 g; 5.4 ml) |
| Batch (C) | |
| 50 mmol | ethyl acrylate (5.01 g; 5.4 ml) |
| 43.2 ml | tert-butanol |
| Batch (D) (according to the invention) | |
| 50 mmol | ethyl acrylate (5.01 g; 5.4 ml) |
| 5 ml | tert-butanol |
| Batch (E) | |
| 50 mmol | ethyl acrylate (5.01 g; 5.4 ml) |
| no tert-butanol | |

In the batches, methyl glucoside was in part present as solid, that is to say the reaction solution is saturated with methyl glucoside.

The conversion rates determined from two identical batches and the reaction conditions used (molar excess of acrylate and solvent fraction) are summarized in the following table 1:

TABLE 1

| Experi-ment | Conditions | | Conversion rate (%) | | |
|---|---|---|---|---|---|
| | Solvent fraction | Acrylate excess | 1st batch | 2nd batch | Mean |
| A | 4.8 ml/mmol | 45× | 52.9 | 54.6 | 53.8 |
| B | 5 ml/mmol | 10× | 32.9 | 32.5 | 32.7 |
| C | 8.6 ml/mmol | 10× | 36.2 | 38.2 | 37.2 |
| D | 1 ml/mmol | 10× | 47.7 | 55.5 | 51.6 |
| E | — | 10× | 13.8 | 13.3 | 13.6 |

The prior art requires an at least 45 fold excess of ethyl acrylate over methyl glucoside with many solvents (batch A; Goede et al. 1993). If the ethyl acrylate excess is reduced to 10 fold, the conversion rate falls as expected. This applies both with the same level of solvent fraction (batch B) and also with increased solvent fraction (batch C). Surprisingly, the reduced conversion rate can be compensated for by decreasing the solvent fraction (batch D). If the solvent is omitted entirely, the conversion rate falls dramatically (batch E).

b) Experiments Using Methyl Acrylate

The same trend as for ethyl acrylate were also found with methyl acrylate. For this, the following batches (F) to (I) were tested.

| Batch (F) to (I): | |
|---|---|
| 5 mmol | methyl α-D-glucopyranoside |
| 50 or 250 mmol | methyl acrylate |
| 5 or 25 ml | tert-butanol |
| 100 mg | Novozym 435 |
| 1 g | 5 Å molecular sieve |

Shake for 24 h at 40° C.
The conversion rate was determined by GC after silylation.

Methyl glucoside was present in part in the batches as solid, that is to say the reaction solution is saturated with methyl glucoside.

The conversion rates determined from two identical batches and the reaction conditions used (molar excess of acrylate and solvent fraction) are summarized in the following table 2:

TABLE 2

| Experi-ment | Conditions | | Conversion rate (%) | | |
|---|---|---|---|---|---|
| | Solvent fraction | Acrylate excess | 1st batch | 2nd batch | Mean |
| F | 5 ml/mmol | 50× | 53.1 | 51.2 | 52.2 |
| G | 5 ml/mmol | 10× | 47.1 | 39.4 | 43.3 |
| H | 1 ml/mmol | 50× | 81.9 | 77.3 | 79.6 |
| I | 1 ml/mmol | 10× | 60.6 | 67.1 | 63.9 |

For a 50 fold excess of methyl acrylate over sugar and 5 ml of tert-butanol per mmol of sugar, a 52% conversion rate is obtained (batch F). If the sugar excess is decreased, the conversion rate falls as expected (batch G). If then the solvent content is also reduced to 1 ml per mmol, the conversion rate surprisingly increased to 64% (batch I, according to the invention). As a result of the reduced amount of solvent, in the case of 50 fold sugar excess, surprisingly, a conversion rate which was increased from 52% (batch F) to 80% (batch H, according to the invention) was also found.

We claim:

1. A process for the enzymatic synthesis of 6-O-acryloyl $C_{1-30}$ alkyl glycosides comprising reacting a $C_{1-30}$ alkyl glycoside compound with an acrylic acid compound or an alkyl ester thereof in a liquid reaction medium comprising a solvent in the presence of an acrylate-transferring enzyme at a temperature suitable for effecting the reaction, thereby producing the 6-O-acryloyl $C_{1-30}$ alkyl glycoside, wherein the solvent is an organic solvent, wherein the organic solvent is present in an amount of 0.01 to 4 ml per mmol of the $C_{1-30}$ alkyl glycoside compound, wherein the acrylic acid compound or the alkyl ester thereof and the $C_{1-30}$ alkyl glycoside compound are in a molar ratio of 10:1 to 3:1; wherein the acrylic acid compound or alkyl ester thereof is selected from the group consisting of acrylic acid, acrylic acid substituted by $C_1$-$C_6$ alkyl groups, and the $C_1$-$C_6$ alkyl esters thereof wherein the enzyme is selected from the group consisting of lipases according to E.C.3.1.1.3 that is free or immobilized in said liquid reaction medium; and wherein the enzyme content in the liquid reaction medium is in the range from 0.1 to 10% by weight of the $C_{1-30}$ alkyl glycoside compound.

2. The process of claim 1, wherein the concentration of the $C_{1-30}$ alkyl glycoside compound is from 0.1 to 20 mol/l.

3. The process of claim 2, wherein the concentration of the $C_{1-30}$ alkyl glycoside compound is from about 0.15 to 10 mol/l.

4. The process of claim 1, wherein the $C_{1-30}$ alkyl glycoside compound is selected from the group consisting of monosaccharides and oligosaccharides that are in optically pure form or a mixture of stereoisomers, and mixtures thereof.

5. The process of claim 4, wherein the oligosaccharides are selected from the group consisting of disaccharides, trisaccharides, and mixtures thereof.

6. The process of claim 4, wherein the monosaccharides are selected from the group consisting of aldoses, ketoses, aldopentoses, ketopentoses, aldohexoses, ketohexoses, alkyl glycosides, and mixtures thereof.

7. The process of claim 1, wherein the organic solvent is selected from the group consisting of $C_3$-$C_6$-alkanols, tert-butanol, tert-amyl alcohol, pyridine, polyalkylene glycol dialkyl ether, alkylene carbonate, $C_3$-$C_6$-alkyl acetate, tert-butyl acetate, acetone, 1,4-dioxane, 1,3-dioxolane, THF, dimethoxymethane, dimethoxyethane and mixtures thereof.

8. The process of claim 1, wherein reacting is at a temperature of from about 0° C. to about 70° C.

9. The process of claim 1, wherein the liquid reaction medium is single-phase or multiphase and the $C_{1-30}$ alkyl glycoside compound and the acrylic acid compound or the alkyl ester thereof are present in dissolved, suspended or emulsified form.

10. The process of claim 1, wherein alcohol produced in the reaction is removed.

11. The process of claim 1, further comprising isolating the 6-O-acryloyl $C_{1-30}$ alkyl glycosides from the reaction medium.

12. A process for making polymeric 6-O-acryloyl $C_{1-30}$ alkyl glycosides comprising:
   a) preparing at least one 6-O-acryloyl $C_{1-30}$ alkyl glycoside by reacting a $C_{1-30}$ alkyl glycoside compound with an acrylic acid compound or an alkyl ester thereof in a liquid reaction medium comprising a solvent in the presence of an acrylate-transferring enzyme at a temperature suitable for effecting the reaction, thereby producing the at least one 6-O-acryloyl $C_{1-30}$ alkyl glycoside, wherein the solvent is an organic solvent, wherein the organic solvent is present in an amount of 0.01 to 4.0 ml per mmol of the $C_{1-30}$ alkyl glycoside compound, wherein the acrylic acid compound or the alkyl ester thereof and the $C_{1-30}$ alkyl glycoside compound are in a molar ratio of 10:1 to 3:1; wherein the acrylic acid compound or alkyl ester thereof is selected from the group consisting of acrylic acid, acrylic acid substituted by $C_1$-$C_6$ alkyl groups, and the $C_1$-$C_6$ alkyl esters thereof wherein the enzyme is selected from the group consisting of lipases according to E.C.3.1.1.3 that is free or immobilized in said liquid reaction medium; and wherein the enzyme content in the liquid reaction medium is in the range from 0.1 to 10% by weight of the $C_{1-30}$ alkyl glycoside compound; and b) polymerizing the at least one 6-O-acryloyl $C_{1-30}$ alkyl glycoside.

13. The process of claim 12, further comprising separating the at least one 6-O-acryloyl $C_{1-30}$ alkyl glycoside from the reaction mixture before the polymerizing step.

14. The process of claim 12, further comprising polymerizing the at least one 6-O-acryloyl $C_{1-30}$ alkyl glycoside together with one or more co-monomers.

15. The process of claim 14, wherein the one or more co-monomers are other 6-O-acryloyl $C_{1-30}$ alkyl glycosides, polymerizable non-sugar co-monomers or both.

* * * * *